US005419756A

United States Patent [19]

McConnell

[11] Patent Number: 5,419,756

[45] Date of Patent: May 30, 1995

[54] ARM TRACTION DEVICE AND METHOD OF USING SAME

[75] Inventor: Bernard E. McConnell, Greenville, Tex.

[73] Assignee: McConnell Orthopedic Mfg. Co., Inc., Greenville, Tex.

[21] Appl. No.: 186,279

[22] Filed: Jan. 24, 1994

Related U.S. Application Data

[63] Continuation-in-part of Ser. No. 908,153, Jul. 2, 1992, which is a continuation of Ser. No. 578,809, Apr. 1, 1991, Pat. No. 5,127,898, which is a continuation of Ser. No. 173,440, Mar. 25, 1988, Pat. No. 5,003,967.

[51] Int. Cl.⁶ ........ A61F 5/048

[52] U.S. Cl. ........ 602/36; 602/21; 602/6; 606/54

[58] Field of Search ........ 602/6, 20, 21, 17, 18, 602/19, 23, 25, 26, 27, 33, 34, 35, 36, 37, 38, 39; 606/54, 55, 56, 57; 248/58, 62, 74.3, 205.2, 231.9

[56] References Cited

U.S. PATENT DOCUMENTS

| | | | |
|---|---|---|---|
| 1,366,612 | 1/1921 | Vallée | 602/33 |
| 2,658,510 | 11/1953 | Hilton | 128/165 |
| 2,808,049 | 10/1957 | Graham | 60/33 X |
| 3,105,972 | 10/1963 | Christopher | 2/161 A |
| 3,274,616 | 9/1966 | Russo | 128/165 |
| 3,348,238 | 10/1967 | Hydock | 128/165 |
| 3,476,108 | 11/1969 | Matukas | 2/158 |
| 3,532,344 | 10/1970 | Massteb | 2/161 A |
| 3,547,112 | 12/1970 | Courtney | 128/77 |
| 3,559,212 | 2/1971 | Skoitron | 2/161 A |
| 3,774,242 | 11/1973 | Owen | 128/77 |
| 3,863,271 | 2/1975 | Moroney | 2/161 A |
| 3,943,923 | 3/1976 | Scheinberg | 602/6 |
| 4,125,257 | 11/1978 | Lew | 128/75 |
| 4,281,647 | 8/1981 | Antypas | 128/77 |
| 4,515,152 | 5/1985 | Teeter | 128/75 |
| 4,698,850 | 10/1987 | Patton | 128/77 |
| 4,702,465 | 10/1987 | McConnell | 269/328 |
| 4,708,510 | 11/1987 | McConnell et al. | 403/90 |
| 4,721,276 | 1/1988 | Moss | 248/205.2 X |
| 4,836,195 | 6/1989 | Berrehail | 602/20 |
| 5,003,967 | 4/1991 | McConnell | 128/77 |
| 5,127,878 | 7/1992 | McConnell | 602/19 |
| 5,269,748 | 12/1993 | Lonardo | 602/6 X |

FOREIGN PATENT DOCUMENTS

| | | | |
|---|---|---|---|
| 1167340 | 5/1984 | Canada | 602/6 |
| 104809 | 3/1917 | United Kingdom | 128/77 |

*Primary Examiner*—Chris A. Bennett
*Attorney, Agent, or Firm*—Dennis T. Griggs

[57] ABSTRACT

A traction bar for use in combination with a hand wrap or hand and arm wraps for suspending and orienting a patient's hand and arm in a substantially elevated position during a surgical procedure and for maintaining a patient's hand and arm in that orientation and location without unduly constricting circulation in the patient's hand or arm. The hand wrap is attached about the patient's closed fist and the traction bar is bendable and includes VELCRO hook material so that the traction bar may be conformed to the hand and attach itself securely in place to the top and two opposing side surfaces of the hand wrapped fist so that rotational or traction forces may be applied to the hand and arm. In this configuration, the lifting and orientation forces do not exert excess pressure at a particular position such as on the patient's wrist, so that the flow of blood to and from the patient's hand and fingers is not constricted. The attachment of the traction bar to the hand and arm wrap provides for substantially complete immobility of the hand and/or arm where enclosed by the wraps, and thus affords stable positioning of the hand or arm during surgery.

4 Claims, 4 Drawing Sheets

ARM TRACTION DEVICE AND METHOD OF USING SAME

CROSS-REFERENCED TO RELATED APPLICATION

This application is a continuation-in-part of application Ser. No. 07/908,153, filed 2 Jul. 1992, which is a continuation of application Ser. No. 07/578,809, filed 1 Apr. 1991, which now is U.S. Pat. No. 5,127,898, which is a continuation of application Ser. No. 07/173,440, filed 25 Mar. 1988 and now is U.S. Pat. No. 5,003,967.

FIELD OF THE INVENTION

This invention is related generally to traction devices for positioning and orienting a body member such as a hand or arm, and maintaining that body member in a specific orientation and position while surgery proceeds.

BACKGROUND OF THE INVENTION

Traction devices are commonly used by surgeons to maintain a limb or extremity in an elevated position during a surgical procedure or during recovery after an operation. For example, if a person has a broken arm, the arm may be elevated by a traction device while the person is reclining on an operating table, in order to immobilize and align the arm such that the fracture may be repaired properly.

DESCRIPTION OF THE PRIOR ART

According to prior practice, traction devices used for maintaining the arm in an elevated position typically include a sling which is secured above the wrist for exerting a lifting force on the arm. The pressure caused by this lifting force is 12 directed inwardly around the patient's wrist, thereby tending to cut off the blood circulation to and from the hand and fingers. The blood circulation problem is aggravated by the fact that the arm is held upright, which makes it necessary for the blood to flow through the arteries of the arm against the force of gravity. Another limitation of the prior art traction devices is that distal portions of the radius and ulna bones (i.e., the two bones of the forearm) in the wrist area are enclosed by the traction device which makes it difficult to gain access to these distal portions if required during a surgical procedure.

There are some traction devices which have localized constriction around the fingers, such as the "Chinese finger trap" devices that cut off blood circulation, and also there are wrist sling devices which apply localized constricting forces about the wrist and cut off circulation through the wrist.

OBJECTS OF THE INVENTION

The principal object of the invention is to provide a hand wrap and traction bar combination which permits traction to be applied as the wrist is manipulated in extension, flexion, ulnar deviation, radial deviation and any combination of these movements.

Another object of the present invention to provide an improved traction and orientation device for retaining the arm and hand of a patient in a stable, elevated position.

Yet another object is to control the various deviations of the wrist while applying traction, and at the same time, permit rotation of the forearm while effecting the foregoing various deviations of the wrist.

A further object of the invention is to provide a hand traction type device which provides sufficient radial clearance around the patient's wrist to allow ready access to distal portions of the forearm bones during a surgical procedure.

SUMMARY OF THE INVENTION

A bendable traction bar is attached to an arm wrap or a hand wrap in a manner which conforms to the general shape of the arm or hand and evenly distributes the applied forces to the hand and/or arm through the wrap itself. A quick release clamp projection of the traction bar is generally centrally located across the top of the fist and thus is substantially aligned with the axis of the wrist and arm. The attachment uses fabric type hook material to secure the traction bar to three separate surfaces of the fist (i.e. the top and both sides of the fist). Forces are applied both vertically and rotationally to the quick release clamp projection. Since the forces transferred to the hand via the conically shaped hand wrap are in general coincident with the axis of the patient's arm, the traction bar provides the ability to precisely orient the hand and arm and to then maintain the desired orientation and location of the arm during surgery while still allowing re-orientation of the hand or arm during surgery when and if required.

In a preferred embodiment of the traction bar, stock may be employed which is wider than it is thick whereby it resists bending in the width plane and yet will bend in a direction vertical to the thickness so that it can be relatively easily be made to conform to the body member being oriented and located. Although the preferred embodiment uses an aluminum stock as a unitary device, the traction bar can also be made of other bendable metals and composite materials, or it can be molded from all synthetic materials, such as plastic or nylon. An advantage of using synthetic materials is that the traction bar can easily be cut to the appropriate length in the operating room and yet, with a secure attachment to the hand wrap, will provide the necessary rotational force resistance to prevent accidental movement of the patient's arm during surgery.

Operational features and advantages of the present invention will be understood by those skilled in the art upon reading the detailed description which follows with reference to the attached drawings.

DETAILED DESCRIPTION OF THE PREFERRED EMBODIMENT

Figure 1:
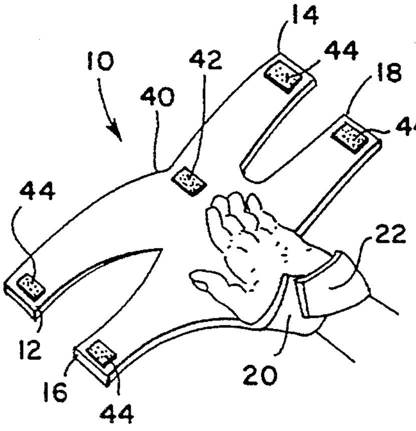
FIGS. 1-4 are perspective views illustrating the procedure by which a hand wrap is applied to a patient's hand to maintain the patient's hand in a closed fist position with the thumb exposed.

In the description which follows, like parts are indicated throughout the specification and drawings with the same reference numerals, respectively. The drawings are not necessarily to scale and the proportions of certain parts may have been exaggerated to better illustrate details of the present invention.

In FIG. 1, a hand wrap 10 is shown with a relatively flat elongated central member 40 and first, second, third, fourth, fifth and sixth relatively flat panels 12, 14, 16, 18, 20 and 22, respectively, which depend outwardly from the central member 40. The central member 40 and the flat panels 12–22 comprise a pile fabric face with a plurality of loop elements. On the distal ends of each of the panels 12–18 and 22 there are pieces of a hook type attachment material 44 which is complementary to the loop elements on the fabric face of the remaining portions of the hand wrap.

When pressing the first and second attachment materials together, there is produced an intermeshing or locking of the hooks and loops to provide a bond of significant strength and shear. Material which is suitable for the first and second attachment materials of the hand wrap end 44 is sold by Velcro Corporation under the trademark "VELCRO". The materials comprising the first and second attachment materials may be switched (i.e., loops can be substituted for hooks and hooks can be substituted for loops).

Although a further attachment 42 of hook material is shown in the center of the distal end of central member 40, it is the same material as 44. The opposing pairs of flat panels cooperate with one another. As will be noted, the commencement of the wrapping process comprises laying the back of the hand on the hand wrap between panels 20 and 22. The patient's hand is positioned such that the wrist of the patient is substantially coterminous with the proximate edge of wrap 10. The first panel is then folded about the wrist and panel 22 is folded on top of panel 20 to engage the loop material on what was formerly the back surface of panel 20 with hook material 44 (not shown) on the distal end of panel 22.

Figure 2:
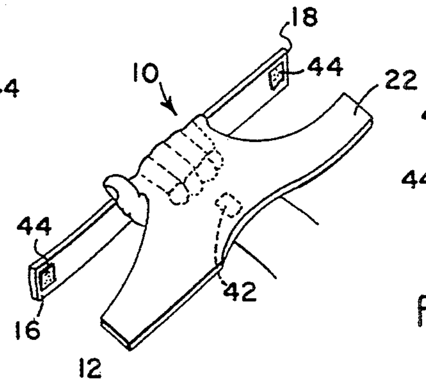
Figure 3:
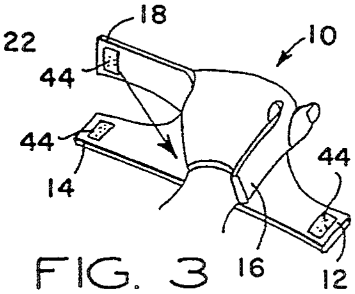
Figure 4:
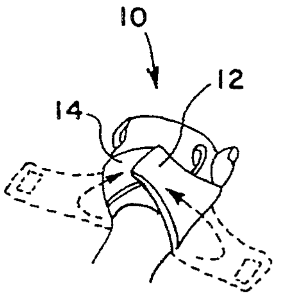

FIGS. 2–4 show the remaining steps for enclosing the hand of the patient in a manner to form the previously mentioned inverted cone. Referring to FIG. 2, the distal end of wrap 10 is then folded over such that the fingers of the hand form a fist with the thumb being exposed between panels 12 and 16. The attachment device 42 secures the distal end of wrap 10 to the back of panel 22.

The hand may be rotated as shown in FIG. 3 such that panels 12 and 14 lay flat while the panels 16 and 18 are engaged to the sides of the panels 20 and 22 near the central member 40. As illustrated, panel 16 is already attached and panel 18 has an arrow to show it is attached.

In FIG. 4 there is an illustration of panel 14 being wrapped to enclose panel 18 and attaching itself to the central member 40 contiguous the back of the hand and panel 12 is attached to the back of panel 14 via attachment means 44. As shown in FIG. 4, the patient's fingers define a closed fist position with the thumb extending outwardly. The panels 12, 14, 16 and 18 maintain the fingers in this flexed position with the flexing occurring at the knuckles.

Figure 5:
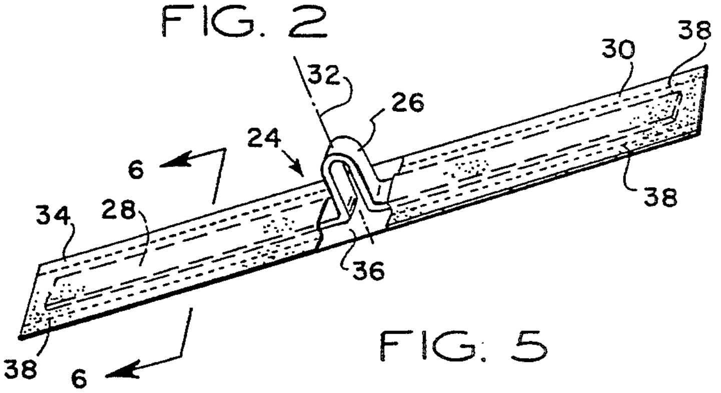
FIG. 5 is a perspective view of a traction bar to be used with the hand wrap of FIG. 4 with the arms of the traction bar in an unmodified or unbent condition.

FIG. 5 illustrates a traction bar generally indicated as 24 having a quick release clamp loop, nipple or projection 26 intermediate arms 28 and 30 extending outwardly from a base of loop 26. In a preferred embodiment, the traction bar comprising elements 26, 28 and 30 may be a bar of aluminum which is sharply bent in three places to form the loop 26. An axis 32 is shown as being centrally located within projection 26 and defines an axis of rotation when rotational forces are applied to the loop or projection 26. A majority portion of the arms 28 and 30 are shown in dashed lines as they are enclosed by two layers of attachment material.

On the upper surface of arms 28 and 30, there is loop type fabric 34, whereas on the lower surface there is hook type fabric 36. Also illustrated is thread or other attachment devices 38 attaching the hook and loop fabric together to fully enclose the arms 28 and 30. Since the hook fabric 36 is continuous for the length of the bar, the fabric cannot easily be disengaged from the bar after being sewn or otherwise attached in place. Further, since the position of thread or other type attachment 38 is immediately adjacent the edges of arms 28 and 30, there can be substantially no rotation of these arms with respect to the attachment material 34 and 36.

Referring to FIG. 5, an axis A extends along the length of the bar 24 from one end of arm 28 to the end of arm 30. Since the bar 24 is much wider than it is thick, it will bend in a first direction (up and down or in the thickness direction) than at 90 degrees to that first direction (sideways or in the width direction). The direction of bending action may also be described by defining an imaginary plane parallel to the widest surface of the bar. The bar is relatively easily bendable in a direction perpendicular to the plane as compared to the resistance to bending in a direction parallel to the plane and at 90 degrees to the other bending direction.

Figure 6:
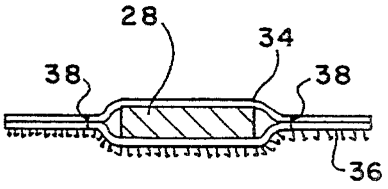
FIG. 6 is a cross-sectional view of one of the arms of FIG. 5.

FIG. 6 shows the arm 28 of traction bar 24 in cross-sectional illustration with an exaggeration of the hooks of hook material 36 on the bottom attached by some device such as thread 38 to the loop type material 34 on the top.

Figure 7:
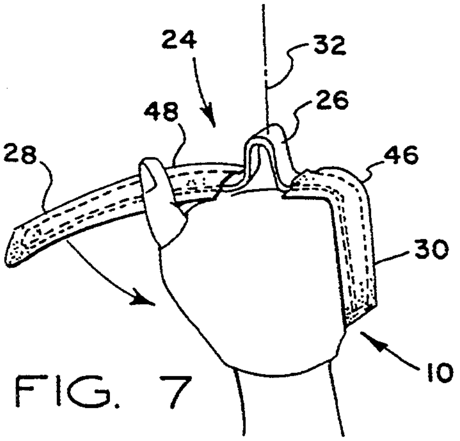
FIG. 7 illustrates the bar of FIG. 5 in partial completion of bending the traction bar to conform to the exterior surface of a hand wrap.

FIG. 7 illustrates that the arms 28 and 30 of the bar may be bent to fit the patient's hand. As illustrated, the arm 30 is bent at 46 and is being bent at 48 to define the width of the patient's hand. The hook type material 36 on the underside of the arms 28 and 30 securely attaches the traction bar 24 to the top of the fist as well as to the sides of the wrap 10 and act to substantially enclose the patient's hand. As will be noted the projection 26 is substantially centered along the top of the patients fist and thus is generally aligned with the axis of the patients arm.

Figure 8:
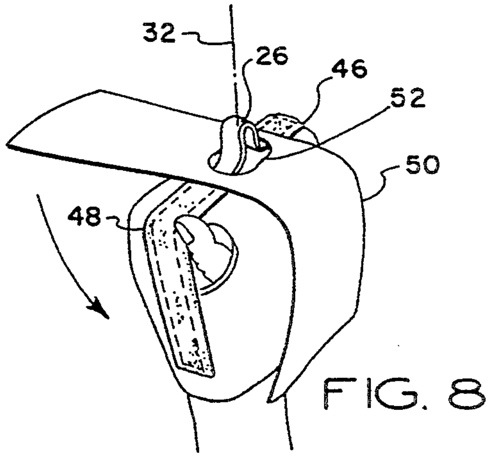
FIG. 8 is a further perspective view showing the apparatus as shown in FIG. 7 with an additional or safety wrap attachment to prevent the accidental release of the traction bar.

While any rotation forces applied around axis 32 through the hook and loop attachment fabric will cause the patient's hand to rotate even where the patient may have the strength to attempt considerable resistance, FIG. 8 illustrates a security or safety wrap 50 further enclosing the traction bar 24 by passing the loop or projection 26 through an opening 52 in a central portion of security wrap 50. Security wrap has hook type material on the underside thereof for secure engagement with the hand wrap 10 of FIG. 7.

Figure 9:
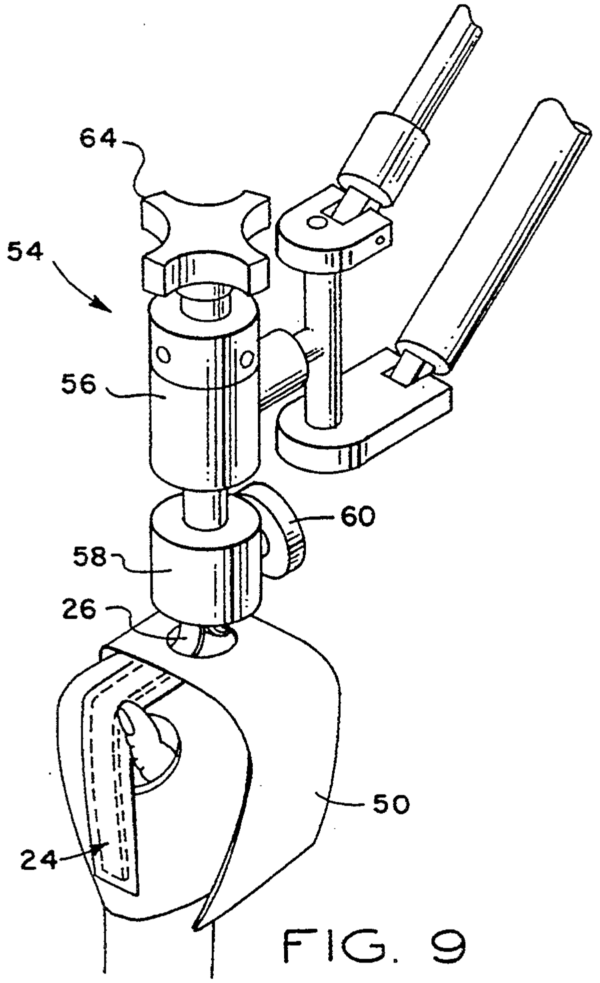
FIG. 9 is a perspective view illustrating an arrangement for attaching the hand wrap of the present invention to a traction support member.

FIG. 9 illustrates a traction support member generally indicated as 54 which is attached to positioning apparatus such as may be found in my U.S. Pat. No. 4,702,465 issued Oct. 27, 1987 and which is incorporated by reference. The traction support member 54 includes a releasable ball clamp assembly 56. The ball clamp assembly 56 is preferably constructed as shown in my U.S. Pat. No. 4,708,510 entitled "Ball Joint Coupling" which is also hereby incorporated by reference. A coupling collar 58 has a compression force knob 60 which has a threaded extension that can be screwed inwardly to a point where it contacts one side of loop or projection 26. This action is also shown in FIGS. 10 and 11.

Figure 10:
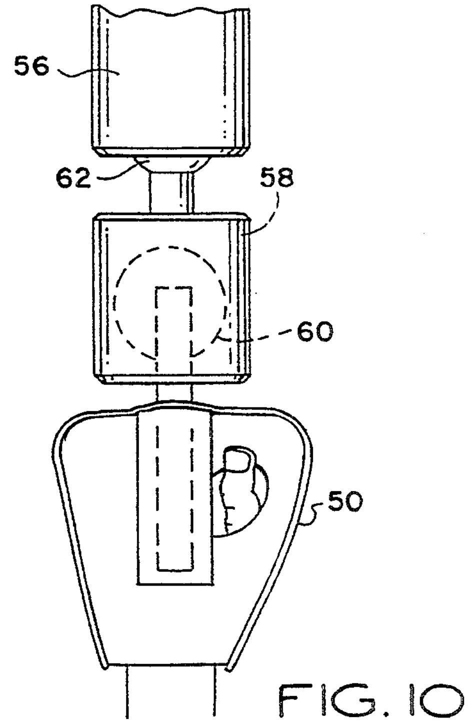
FIG. 10 is a perspective and more detailed view of the clamp arrangement for the traction bar of FIG. 9.

FIG. 10 additionally shows a ball 62 which allows the coupling collar 58 to be rotated along with a rotation of the patient's hand to any position as long as a handle 64 is loosened. When handle 64 is tightened, the ball 62 can no longer rotate, and thus neither can the coupling 58 or the hand within wrap 10.

Figure 11:
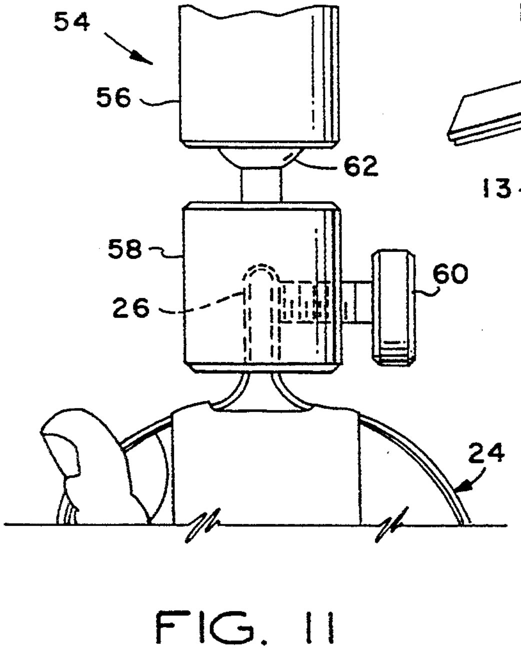
FIG. 11 is a view of the clamping approach at a 90 degree rotation from that of FIG. 10.

FIG. 11 is a side view of the loop 26 while FIG. 10 presents an end view of loop 26 with the handle 60 in dashed line format to illustrate that it is hidden from view at the back of the collar 58.

The ball member 62, when released from pressure by handle 64, can be rotatably moved as can the entire support member 54 to manipulate the patient's hand relative to the wrist in extension, flexion, ulnar deviation, radial deviation, or any combination of those movements, while applying traction through the hand and wrist. Further, the traction bar 24, by partially enclosing the patient's hand on three sides and the secure attachment thereof to the wrap 10, prevents any substantial movement in a rotational direction about the axis 32 of the loop 26. According to this arrangement, traction and orientation forces applied by the traction support member 54 are efficiently transmitted through the clamp assembly 58 to the hand traction wrap 10 and, accordingly, in a distributed manner to the patient's fist.

As illustrated, traction is applied to an inverted conical surface which the fist presents whenever the fingers are fully flexed at the knuckles. After a fist has been made, an inverted conical surface is produced that transitions gradually from the wrist upwardly to the proximate knuckles. Additionally, after the wrap has been secured in place about the conical surface of the fist, the wrap 10 maintains the fist in the closed position, and prevents the hand from opening while it is being held in a suspended orientation.

The wrap 10 and the associated traction bar 24 distributes the traction forces across the conical surface of the closed fist with the forces being applied onto the wrap being relatively smaller near the junction of the wrist and becoming relatively greater in magnitude toward the top of the fist. The radially inwardly directed forces which prevent the wrap from being pulled off the wrist are applied through the wrap rather than being focused on the wrap or some other localized point of application. The traction force applied to the wrap through the bar 24 and its associated hook attachment material 36 produces a shear force along the conical surface of the closed fist.

Figure 12:
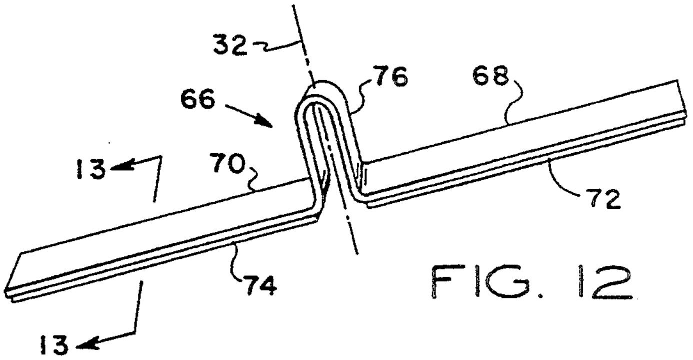
FIG. 12 illustrates one configuration of a traction bar to be used in maintaining orientation and location of the forearm in addition to the hand.

FIG. 12 illustrates an arm traction bar 66 having extensions 68 and 70. Extensions 68 and 70 are similar to arms 28 and 30 of FIG. 5 except that when traction bar 24 of FIG. 5 is used with a hand, the extensions are substantially identical in length on either side of the projection 26. The traction bar of FIG. 12 is for use in manipulating the arm of a patient and as will be seen from further figures, the arm or extension 70 is much longer than extension 68. The traction bar 66 would still, in a preferred embodiment, be made of bendable aluminum. The bar 66 incorporates hook attachment material 74 on the undersurface of extension 70 and hook attachment material 72 on the undersurface of extension 68. This is more clearly shown in FIG. 13.

Figure 13:
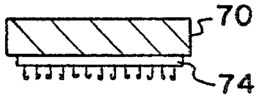
FIG. 13 is a cross-section of a portion of FIG. 12.

While the attachment material in the preferred embodiment will be used on traction bar 66 in the same manner as shown in FIG. 5, the alternate embodiment illustrated in FIGS. 12 and 13 is utilized to more clearly show the use of the arm traction bar in the following figures. The very large amount of hook attachment surface provides sufficient shear strength that the preferred embodiment, as illustrated in FIG. 5, is not necessary in all instances. However, it is to be understood that either embodiment falls within the scope of the invention.

Figure 14:
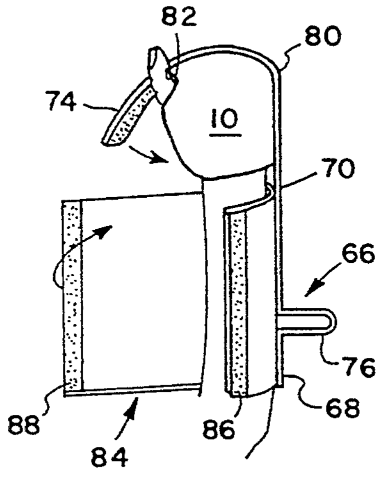
FIG. 14 is a perspective view illustrating an arm wrap being applied in addition to the hand wrap and the partial installation of the traction bar to both of these wraps.

As illustrated in FIG. 14, a patient's hand is enclosed by wrap 10 as previously shown in FIGS. 1 through 4. The patient's arm is then enclosed in a further wrap 84 which may be generally comprised of loop type wrap material with hook type attachment materials 86 and 88 as shown. When the wrap is used to enclose the forearm as shown, the attachment material 86 will contact the underside of the wrap 84 and the attachment material 88 will attach to the upper surface of the wrap to securely encase the patient's arm. The hook type material on the underside of traction bar 66 will then adhere to the loop material of wrap 84.

The traction bar extension 70 may be bent at points 80 and 82 to enclose the fist with the hook type attachment material shown on the underside of the distal end 74 of extension 70. Referring to FIG. 14, the end 74 of bar 70 is being bent at point 82 to conform to the shape of the wrap 10 at the thumb side of the patients fist, with a large amount of surface being presented for attachment. Although a patient is unlikely to exert any resistive forces to movement or orientation of traction bar 66, the shear forces involved in the hook and loop material is substantial and with the wrapping of the extension 70 around the fist, the traction bar 66 is well attached to the patient's arm and does not allow any movement of the arm or hand while still distributing all the forces over a wide area so that no single area of the arm or hand has undue constrictive forces.

Figure 15:
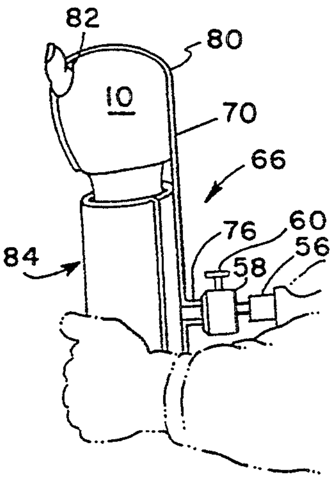
FIG. 15 is a perspective view of the traction bar of FIG. 14 attached to a traction support member.

FIG. 15 shows the patient's arm with the traction bar 66 attached to wraps 10 and 84 and with the loop or projection 76 inserted in the coupling collar 58. The compression force knob 60 is tightened to secure the loop 76 within the coupling collar. The items 56–60 may be the same as illustrated in conjunction with FIGS. 9–11.

Figure 16:
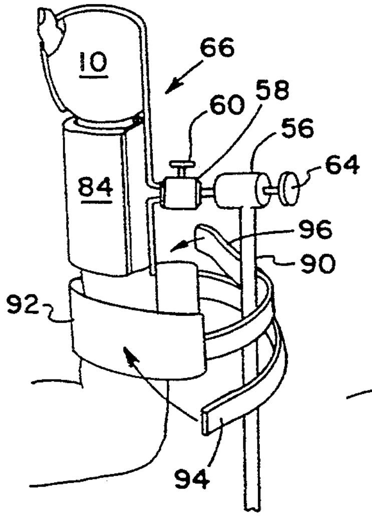
FIG. 16 illustrates the view of FIG. 13 with additional, but non-constricting, support between the patient's arm and the traction support member to prevent the accidental dislodgment of the traction bar from the hand and arm wrap.
Figure 17:
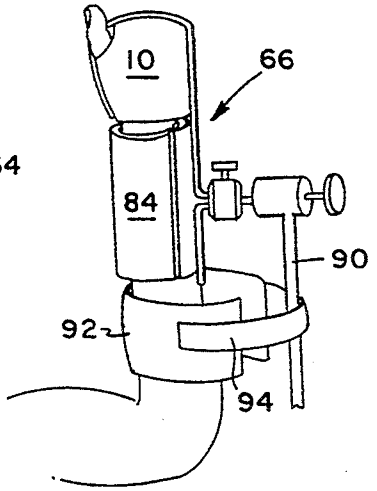
FIG. 17 illustrates a completion of the securing process of FIG. 16.

FIG. 16 shows the arm and hand wrap of FIG. 15 attached to a traction support and orientation device having a movable member 90 used to generally position the ball clamp assembly 56 and the patient's arm. Movable support 90 is part of the universal extremity positioner of my U.S. Pat. No. 4,702,465 and merely illustrates a different intermediate member as compared to that shown in FIG. 9. As illustrated, a further security wrap 92 having attachment tabs 94 and 96 is used to secure a portion of the patient's arm adjacent the elbow to the support 90. While the further security wrap 92 is optional, it provides additional assurance that the orientation provided by the ball clamp assembly 56 will be maintained. FIG. 17 illustrates the wrap 92 with the tabs 94 and 96 secured thereto using attachment hook material of the type previously indicated.

Figure 18:
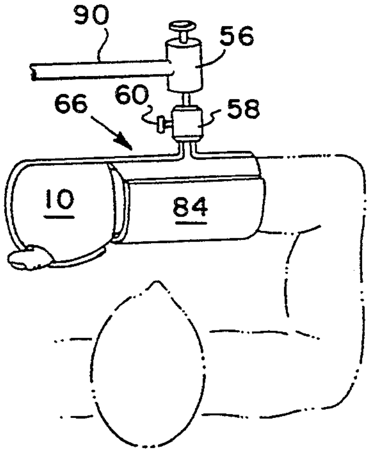
FIG. 18 illustrates the concept of FIG. 15 where a patient is in position to increase surgical access about the elbow.

FIG. 18 illustrates the use of the arm traction bar 66 as secured to the hand wrap 10 and the arm wrap 84 with the patient's arm in position for elbow and arm surgery. By manipulating the arm or support rod 90 along with the ball clamp assembly 56, the arm can be positioned to enable control of elbow flexion-extension, pronation-supination, varus-valgus and rotation.

Figure 19:
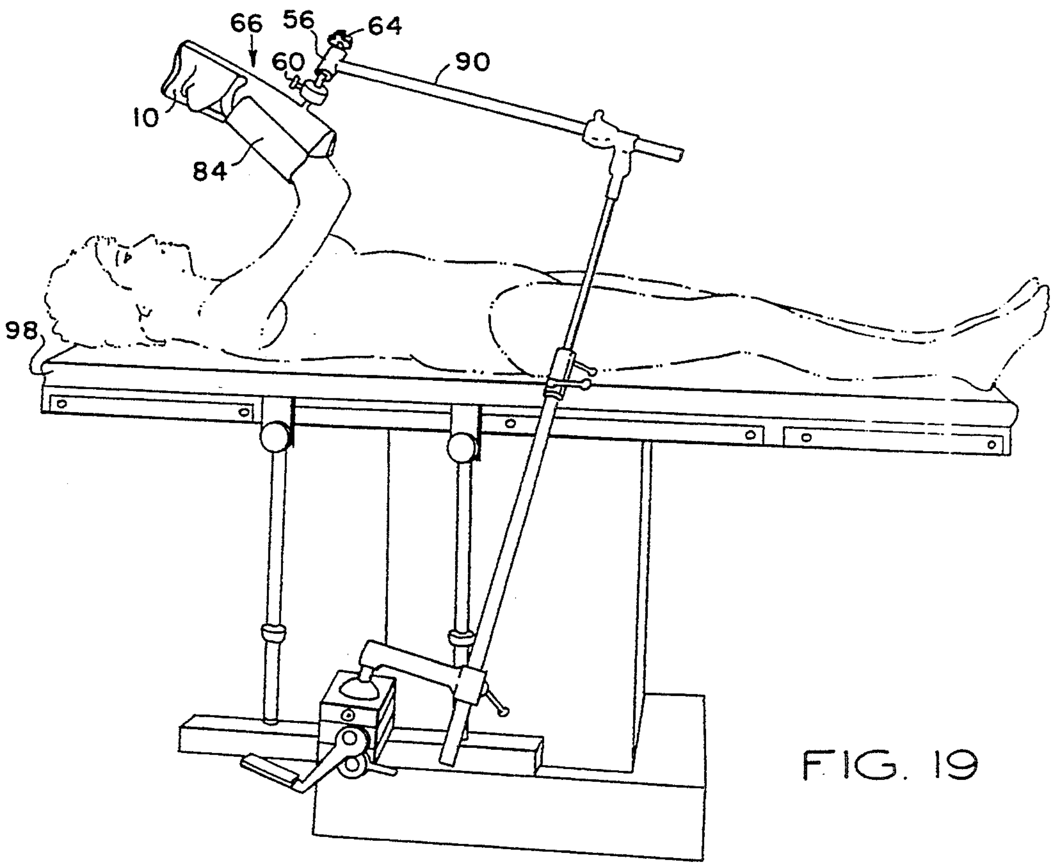
FIG. 19 is a perspective view of a patient on an operating table with the support apparatus and traction bar in place to facilitate access to the patient for elbow and upper arm surgery.

FIG. 19 shows a patient on an operating table 98 and a simplified version of the universal extremity positioner constructed according to my U.S. Pat. No. 4,702,465. As will be apparent from a reading of the patent or from observation of FIG. 19, the various members of the traction support culminating in support 90 can be moved in rotation, height and extension to orient the patient's arm or hand in any desired manner. FIG. 19 in essence shows a side view of what is shown in FIG. 18 as a view from the head of the patient.

Figure 20:
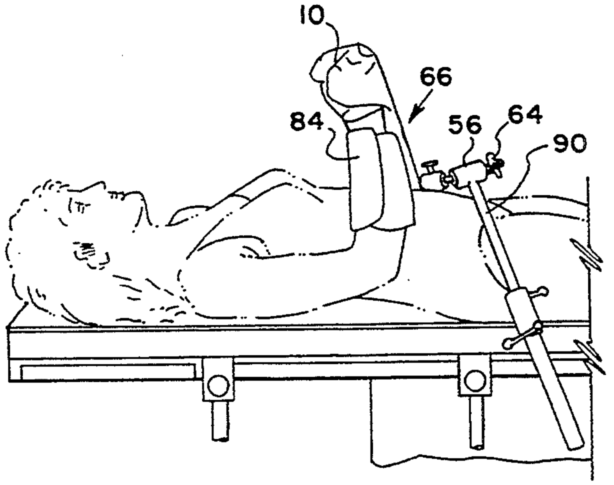
FIG. 20 is a view of a patient with the traction apparatus holding the arm in position for precisely controlling rotation, abduction-adduction and flexion-extension preparatory to shoulder surgery.

FIG. 20 illustrates the arm traction device of FIG. 12 holding the patient's arm in position for shoulder surgery. The support and attendant traction bar, along with the ball clamp assembly 56, allow precise control of rotation, abduction-adduction and flexion-extension. It further allows traction as necessary and appropriate.

Figure 21:
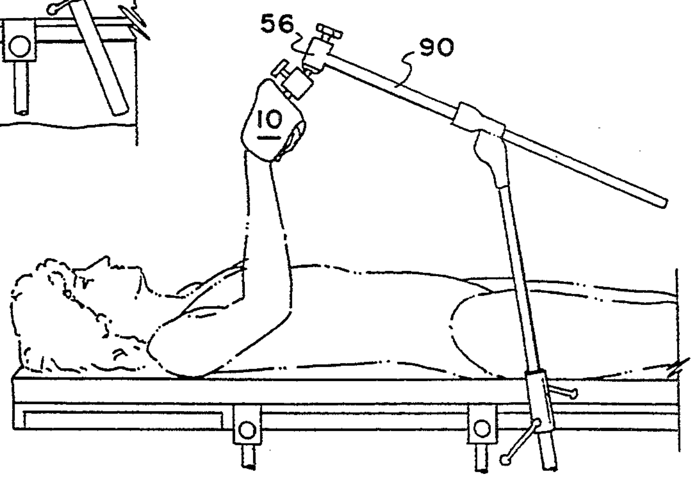
FIG. 21 illustrates the traction support apparatus orienting and locating the patient's hand for wrist and forearm surgery.

FIG. 21 illustrates the present invention where only the hand wrap 10 is used along with the hand traction bar 24 of FIG. 5 and the traction support, including the ball assembly 56 and support device 90, to position the patient's wrist and forearm for surgery. The versatility of this concept allows control of pronation-supination, radial-ulnar deviation, and wrist flexion-extension.

While the preferred embodiment of the invention uses a aluminum bar which has been pre-shaped to include a loop of material used for insertion into a coupling collar whereby rotational forces may be applied to the traction bar and through attachment forces of "VELCRO" type material to wraps on the arm and hand, the traction bar 24 could be made of other material, such as plastic or nylon, and also could be molded rather than bent as illustrated.

Further, while the preferred embodiment provides for attachment to the top of the fist portion of the hand wrap 10 by the hook material of the bar 24 as well as to both the thumb and little finger sides of the fist hand wrap 10, the concept will still perform satisfactorily with the traction bar 24 attached to just the sides of the fist. Also although the preferred embodiment has fabric attached to the traction bar extensions, the invention may be practiced by 1) positioning the traction bar and it's bent extension adjacent the wrapped fist in a manner similar to that shown in FIG. 7 and then 2) wrapping the already enclosed fist and the traction bar with more fabric to assure that the traction bar doesn't rotate relative the fist when rotational forces are applied to the projection 26.

Accordingly, various embodiments of the invention have been described in detail, modifications to the preferred embodiment may be made without departing from the spirit and scope of the invention. The invention is not limited to such details except as set forth in the appended claims.

What is claimed is:

1. The method of orienting and then maintaining a patient's arm and fist in a desired elevation and orientation comprising the steps of:

initially enclosing the patient's hand in a fabric wrap wherein the fingers are bent to form a fist, the fabric wrap having a surface portion which is releasably engagable with one of complementary hook and loop type fastener devices;

conforming first and second bendable bars, extending in opposite directions from a base of a quick release projection, about the patient's enclosed fist;

securing attachment fabric, complementary in type to the fist enclosing wrap, to said first and second bendable bars for facilitating attachment of said bars to the fist enclosing wrap; and, securing said first and second bendable bars to said fist enclosing wrap in such a manner that there is no substantial deformation of said bars when vertical or rotational forces are applied to said quick release projection.

2. The method of claim 1 wherein the attaching step further comprises enclosing said first and second bars by attaching a security wrap to the wrap enclosing the patient's hand which security wrap includes an opening for receiving said projection therethrough.

3. The method of claim 1 comprising the additional steps of:

inserting the quick release projection into an orientation and holding clamp; and moving the holding clamp horizontally, vertically and in rotation until the patient's body member is supported in a desired orientation and elevation.

4. An angle orientation device for use with traction apparatus whereby a patient's body member is held in an elevated and specifically oriented position comprising, in combination:

unitary stock of manually formable material having a U-shaped bend and having first and second ends initially extending in diametrically opposed directions from the U-shaped bend, the U-shaped bend serving as a traction clamp engageable nipple; and body member wrap means for acting in concert with said unitary stock as bent to conform with the body member to first enclose the body member and then secure said stock to said body member to form a body member angle orientation holding device, the holding device acting to hold the body member in a specifically oriented position and elevation when said traction clamp engageable nipple is inserted in and clamped to traction apparatus adapted for holding same.

* * * * *